United States Patent [19]

Williams

[11] Patent Number: 4,901,732
[45] Date of Patent: Feb. 20, 1990

[54] DELTA CUFF

[76] Inventor: Richard B. Williams, 1733 La Senda Pl., South Pasadena, Calif. 91030

[21] Appl. No.: 144,203

[22] Filed: Jan. 15, 1988

[51] Int. Cl.$^4$ .............................................. A61B 5/02
[52] U.S. Cl. .................................... 128/686; 606/202
[58] Field of Search ........ 128/686, 672, 677, 680–685, 128/327

[56]  References Cited

U.S. PATENT DOCUMENTS

| | | | |
|---|---|---|---|
| 1,667,409 | 4/1928 | Barr | 128/686 |
| 2,161,393 | 6/1939 | Tye | 128/327 |
| 2,758,593 | 8/1956 | Berman | 128/686 |
| 2,981,251 | 4/1961 | Berman | 128/686 |
| 3,258,009 | 6/1966 | London | 128/686 |
| 3,504,675 | 4/1970 | Bishop, Jr. | 128/327 |
| 3,670,735 | 6/1972 | Hazlewood | 128/327 |
| 3,765,405 | 10/1973 | Natkanski | 128/686 |
| 4,206,765 | 6/1980 | Huber | 128/686 X |
| 4,572,205 | 2/1986 | Sjonell | 128/686 |
| 4,716,906 | 1/1988 | Ruff | 128/686 |

Primary Examiner—Angela D. Sykes
Attorney, Agent, or Firm—Nilsson, Robbins, Dalgarn, Berliner, Carson & Wurst

[57] ABSTRACT

A sphygmomanometer which is constructed of an inflatable bladder having relatively converging sides arranged so that inflatable converging sides are held in place overlying an artery in the limb of a patient while the bladder may be inflated to measure the blood pressure of the patient.

8 Claims, 1 Drawing Sheet

DELTA CUFF

FIELD OF THE INVENTION

This invention relates to blood pressure monitoring and more particularly to a non-invasive monitor which utilizes a portable sphygmomanometer cuff or band which automatically accommodates to various limb sizes.

BACKGROUND OF THE INVENTION

In measuring the blood pressure of individuals, an air inflatable cuff or band in almost all cases is applied about the upper arm in a region overlying the brachial artery. During the blood pressure measurement, the sleeve is inflated to a pressure lying above systolic pressure and then slowly vented. In that case, Korotkoff tapping sounds are detected with the device such as a stethoscope applied to the brachial artery below the blood occluding portion of the cuff. As is well known, detection of the first Korotkoff sounds and then detection of the sounds becoming muffled or ceasing indicate, respectively, the systolic and diastolic blood pressure of the patient.

At the present time a standard cuff or band having a width of about 12 centimeters is used in almost all instances irrespective of the build or size of the patient. It is well known at the present time that because of the existence of soft tissue between the blood vessel and the bone in the limb (arm or thigh) the real blood pressure measured with the same cuff is ambiguous for different arm thicknesses despite the same pressure being indicated on the manometer. In fact, tests have indicated that errors in the order of 5-10 mm. Hg., and sometimes considerably greater, may exist as to both the systolic and diastolic pressures. Such an error may in some instances be quite decisive as to whether a patient is considered sick or not sick and is to be treated or not treated.

To overcome this error it has been determined that the width of the distensible part of the bladder overlying the artery should be approximately 40% of the circumference of the limb to properly occlude the artery. The American Heart Association (AHA) has recommended a total of seven different cuff sizes to cover a range of arm widths from pediatric to large adult with a plus or minus 5% error. In carrying out the recommendations the individual taking the blood pressure measurement would first have to measure the arm of the patient and then choose the appropriate cuff. It is widely known that such a procedure is not used in a vast majority of wards or clinics or physicians offices. The standard 12 centimeter cuff is instead used in virtually all blood pressure measurements with the attendant inaccuracies.

To solve this problem, blood pressure measuring equipment has been provided to automatically compensate for the varying arm sizes through the medium of providing cuffs with portions thereof which may be selectively inflated while throttling other portions to thus accommodate varying sized arms of patients. Such structures are shown in U.S. Pat. Nos. 3,812,844, 3,906,937, and 4,572,205.

An additional problem attendant measurement of blood pressure exists where the extensible bladder of the cuff or band passes around the arm of the patient. It is recognized that if the distensible bladder extends around the patients arm circumference only once, the likelihood of a more accurate measurement is enhanced. Solutions to this problem by way of inflating only that portion of the bladder which surrounds the patients arm a single time is shown in U.S. Pat. Nos. 1,288,130 and 1,857,567 each of which enables inflation of only a portion of the bladder.

In addition to the foregoing, U.S. Pat. No. 4,501,280 discloses an automated system including appropriate sensors and a microprocessor for automatically measuring the blood pressure while using different size cuffs ranging from conventional to neonatal depending upon patient size.

SUMMARY OF THE INVENTION

The present invention includes a sphygmomanometer having an inflatable bladder including two portions one of which has side edges which relatively converge in a manner such that when the bladder is placed upon the limb of a patient the converging side portion extends over an artery. Means is included for inflating and deflating the bladder and for measuring the blood pressure.

In accordance with a more specific aspect of the present invention, a clamp is provided disposed to receive the bladder to throttle the excess thereof which does not encircle the limb of the patient.

DETAILED DESCRIPTION OF THE INVENTION

A sphygmomanometer constructed in accordance with the principles of the present invention is used in the traditional manner as above described. The various details and components required for operation of a sphygmomanometer are useful in connection with the present invention and are well known to those skilled in the art. Such traditional components and the details with regard to them are not shown except in broad schematic representation or described in the following specification since they are well known.

Figure 1:
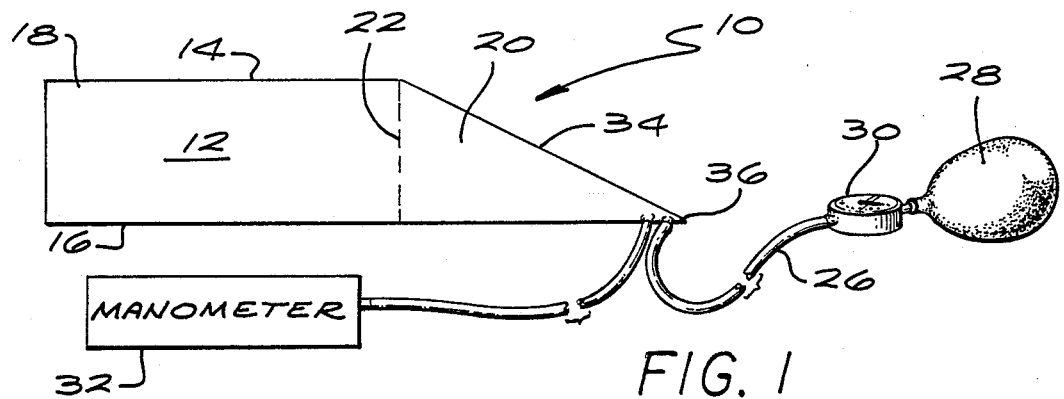
FIG. 1 is a schematic view of a sphygmomanometer constructed in accordance with the principles of the present invention.

Referring now to the drawings and more particularly to FIG. 1, there is schematically illustrated a sphygmomanometer constructed in accordance with the present invention. The sphygmomanometer as illustrated automatically results in placing the tapered inflatable part thereof over the artery in the limb of the patient. The rate of taper is chosen such as to substantially eliminate the errors hereto for attendant blood pressure measurements resulting from the use of a standard cuff irrespective of patient size. Base upon the American Heart Association study, the taper is such that the width of the inflatable portion of the artery is approximately 40% of the circumference of the limb. For purposes of ease in description of the invention the remainder of the description will be given in conjunction with the utilization of the sphygmomanometer on an arm of a patient and in conjunction with the brachial artery.

As is shown in FIG. 1, the sphygmomanometer 10 includes an elongated bladder 12 having sides 14 and 16. The bladder 12 is divided into sections 18 and 20 separated about a medial line 22 thereof. The medial line 22 is shown dashed in FIG. 1 to merely indicate the position of division of the two portions 18 and 20 and does not exemplify a seal or break in the bladder 12. Tubes 24 and 26 are affixed to the bladder 12 as is well known in the art and also may be formed as a single tube as is well known. Preferably the tubes 24 and 26 (or single tube) should be located as near as possible to the vertex. A bulb 28 with appropriate valve 30 is used to inflate and deflate the bladder 12. The well known manometer apparatus 32 is connected to the tube 24 to measure blood pressure of the patient.

As is shown in FIG. 1, the side edges 14 and 16 in the portion 20 of the bladder converge relative to each other. As is shown the side edge 14 slopes as is illustrated at 34 starting at the medial line 22 until it converges with the edge 16 at the vertex 36.

Figure 4:
FIG. 4 illustrates in partial cross section an alternative embodiment of a sphygmomanometer constructed in accordance with the principles of the present invention.

If desired, the bladder 12 may be contained within a non-distensible fabric cover 35 as shown more specifically in FIG. 4.

Figure 2:
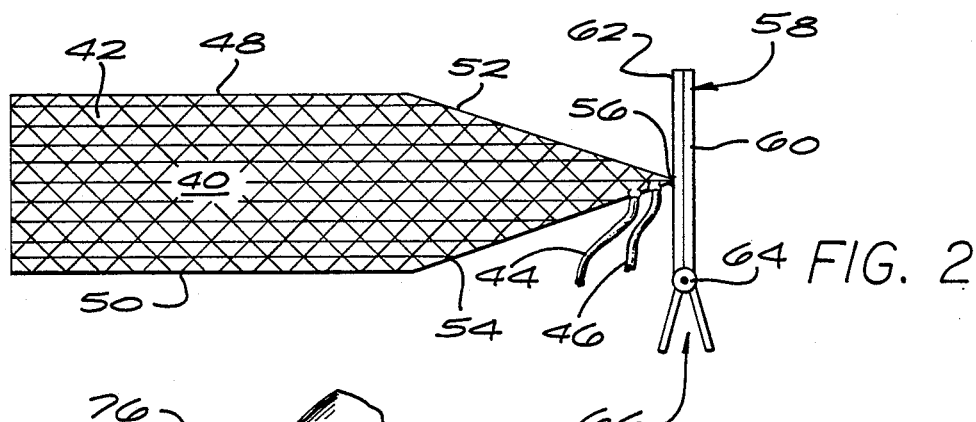
FIG. 2 is a plan view of an alternative embodiment of a sphygmomanometer of the present invention.

Referring now more particularly to FIG. 2, an alternative embodiment of the sphygmomanometer is illustrated. As is therein shown the bladder 40 may have one surface 42 thereof containing a non-distensible matrix as is illustrated by the cross hatching on the surface 42. Such a matrix may be woven ire material constructed of metal or plastic which may be overlaid, adhered to the surface 42 of the bladder 40 along the surface 42. In any event, the non-distensible material functions in the same manner as does the non-distensible cloth cover 34 as shown in FIG. 4 as is well known in the art. Again appropriate tubes 44 and 46 (or a single tube) are affixed to the bladder 40 as is well known and function as above described.

In the embodiment shown in FIG. 2, it will be noted that side edges 48 and 50 converge as shown at 52 and 54 to an apex 56. In this instance, both of the side edges 48 and 50 converge toward each other in such a manner as to provide the relationship above referred to. Clamping means 58 are permanently affixed to the bladder 40 (or alternatively through the combination of the bladder and a cover) as may be desired. The clamping means 58 contains members 60 and 62 which pivot about a point 64 upon the application of pressure to the handle 66 to provide a jaw which may grip or clamp the bladder 40 as will be more fully described below.

Figure 3:
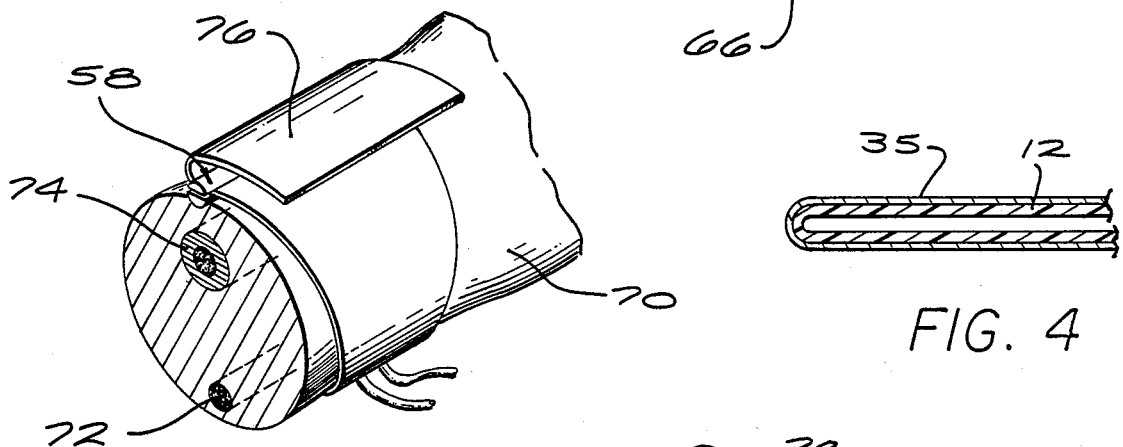
FIG. 3 illustrates a device of the present invention in place upon an arm of a patient.

As is shown in FIG. 3, a patient's arm 70 includes the brachial artery 72 and the lateral epicondyle bone 74. It will be recognized by those skilled in the art that the brachial artery is almost exactly 180 degrees around the arm from the lateral epicondyle. In practice utilizing the sphygmomanometer of the present invention the vertex of the bladder is located proximal the lateral epicondyle after which the bladder is wrapped around the arm 70 of the patient. Preferably, the handle 66 of the clamping means 58 is squeezed together causing the members 60 and 62 to open after which that portion 76 of the bladder which does not encircle the arm 70 of the patient is throttled by the clamping action of the jaws formed by the members 60 and 62. In this manner, the bladder is held securely about the arm 70 of the patient and only that portion of the bladder opposed the circumference of the arm need be inflated by squeezing the bulb 28.

An important aspect of the present invention is that the convergence of the sides of the bladder is such that, that portion of the bladder overlying the brachial artery is always the proper proportion of the circumference of the arm of the patient to provide accurate blood pressure measurement irrespective of the size of the patient's arm. As above pointed out, based on the AHA study, this proportion should be approximately 40% of the circumference of the patient's arm. It has been found that the medial line between the two portions of the bladder such as shown at 18, 20, and 22 in FIG. 1 is approximately half the overall length of the bladder. In this manner, the increase in width of the bladder from the apex does not necessarily have to continue to increase. If the width continues to increase by continuing the slope of the side edges, the overall width of the cuff would become extremely cumbersome and difficult to handle. It has also been found that even though the convergence of the sides commences only at about the middle portion of the bladder, the tapered portion as shown at 20 in FIG. 1, for example, would always overlie the brachial artery.

The important aspect of the present invention is that the taper of that portion of the bladder which overlies the brachial artery is such that, when the vertex is positioned proximal the lateral epicondyle bone, the width of the bladder is approximately 40% of the circumference of the arm of the patient. In this manner, a single sphygmomanometer can be utilized to accurately monitor the blood pressure of a wide range of patients from small children to adults accurately.

Although the preferred embodiment of the present invention includes the clamping means 58, it should be expressly understood that a structure such as that shown in FIG. 1 without the clamping means may also be utilized by employing the traditional fastening devices on a fabric envelope or cover such as Velcro, as is well known in the art. In such an instance, the vertex 36 would be positioned adjacent the lateral epicondyle bone and the bladder or cuff wrapped around the arm of the user and fastened in place after which the blood pressure of the patient would be monitored or measured in the traditional fashion.

Figure 5:
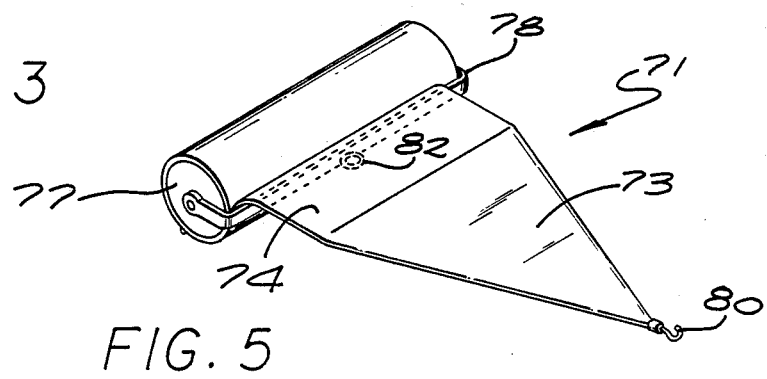
FIG. 5 is an alternative embodiment of the present invention shown in schematic perspective view.

An alternative embodiment of the present invention is illustrated in FIG. 5 to which reference is hereby made. As is therein shown the cuff 71 includes an inflatable portion 73 and may have a non-inflatable portion 74 wound upon a roller 77 having a clamping mechanism 78 extending therefrom. A hook like member 80 attaches to a receiver 82 affixed to the clamp 78 as shown in dashed lines on the reverse side of the cuff from that shown. In practice the cuff is placed on the arm of the patient so that the tapered inflatable portion overlies the tracheal artery in the manner above described. Although a straight taper has been shown and described, it should be understood that the term taper or convergence used throughout is intended to mean and include a variation in width of the single inflatable portion of the cuff overlying the artery to obtain the desired proportion to the limb circumference above described irrespective of how such width variation is achieved.

What is claimed is:
1. A sphygmomanometer comprising:
   a. elongated bladder means for encircling the limb of a patient having first and second portions, one of said first and second portions having relatively converging sides with the convergence commencing at approximately midpoint of said bladder means and terminating at an apex;

b. means for inflating and deflating at least a portion of said bladder means including said relatively converging sides;

c. means for affixing said bladder means to a limb of a patient with said relatively converging sides overlying an artery in the limb of the patient;

d. said convergence being such that when said apex is disposed proximate said patient's lateral epicondyle bone the width of said bladder means at said patient's brachial artery is equal to substantially forty percent (40%) of the circumference of said patient's arm; and e. means connected to said bladder means for measuring the blood pressure of said patient.

2. A sphygmomanometer as defined in claim 1, which further includes means for decreasing compliance of said bladder means.

3. A sphygmomanometer as defined in claim 2, wherein said compliance decreasing means includes a substantially non-distensible fabric cover for said bladder means.

4. A sphygmomanometer as defined in claim 2, wherein said compliance decreasing means includes a substantially non-distensible material formed as an integral part of said bladder means.

5. A sphygmomanometer as defined in claim 1, which further includes clamping means affixed to said converging sides at a terminus thereof.

6. A sphygmomanometer as defined in claim 5, wherein said clamping means defines jaw like members between which the bladder means is received to prevent inflation of that portion of the bladder means not surrounding a patient's limb.

7. A sphygmomanometer as defined in claim 1, which further includes roller means for receiving said bladder means, said roller means including clamping means receiving said bladder means to prevent inflation of that portion of the bladder not surrounding a patient's limb.

8. A sphygmomanometer as defined in claim 7, which further includes hook means at a terminus of said converging sides for securing said bladder means to patient's said limb.

* * * * *